United States Patent
Do et al.

(10) Patent No.: US 6,175,417 B1
(45) Date of Patent: Jan. 16, 2001

(54) METHOD AND APPARATUS FOR DETECTING DEFECTS IN THE MANUFACTURE OF AN ELECTRONIC DEVICE

(75) Inventors: Douglas Do; Ted Taylor, both of Boise, ID (US)

(73) Assignee: Micron Technology, Inc., Boise, ID (US)

( * ) Notice: Under 35 U.S.C. 154(b), the term of this patent shall be extended for 0 days.

(21) Appl. No.: 09/532,869

(22) Filed: Mar. 22, 2000

Related U.S. Application Data

(62) Division of application No. 09/023,925, filed on Feb. 13, 1998.

(51) Int. Cl.$^7$ ..................................................... G01B 9/08
(52) U.S. Cl. ....................... 356/392; 356/388; 356/393; 356/394
(58) Field of Search ................................... 356/388, 392, 356/393, 394, 395

(56) References Cited

U.S. PATENT DOCUMENTS

| | | |
|---|---|---|
| 4,556,317 | 12/1985 | Sandland et al. . |
| 4,794,646 | 12/1988 | Takeuchi et al. . |
| 5,057,689 | 10/1991 | Nomura et al. . |
| 5,109,430 | 4/1992 | Nishihara et al. . |
| 5,555,319 | 9/1996 | Tsubusaki et al. . |
| 5,641,960 | 6/1997 | Okubo et al. . |
| 5,659,172 | 8/1997 | Wagner et al. . |

Primary Examiner—Frank G. Font
Assistant Examiner—Reginald A. Ratliff
(74) Attorney, Agent, or Firm—Dickstein Shapiro Morin & Oshinsky LLP

(57) ABSTRACT

The invention provides a unique method and apparatus for detecting defects in an electronic device. In one preferred embodiment, the electronic device is a semiconductor integrated circuit (IC), particularly one of a plurality of IC dies fabricated on a wafer of silicon or other semiconductor material. The defect detection operation is effectuated by a unique combination of critical dimension measurement and pattern defect inspection techniques. During the initial scan of the surface of the wafer, in an attempt to locate the appropriate area for a critical dimension (CD) feature or element that is to be measured, a "best fit" comparison is made between a reference image and scanned images. The critical dimension measurements are conducted on a "best fit" image. In addition, a "worst fit" comparison is made between the reference and scanned images. A "worst fit" determination represents pattern distortions or defects in the ICs under evaluation.

3 Claims, 9 Drawing Sheets

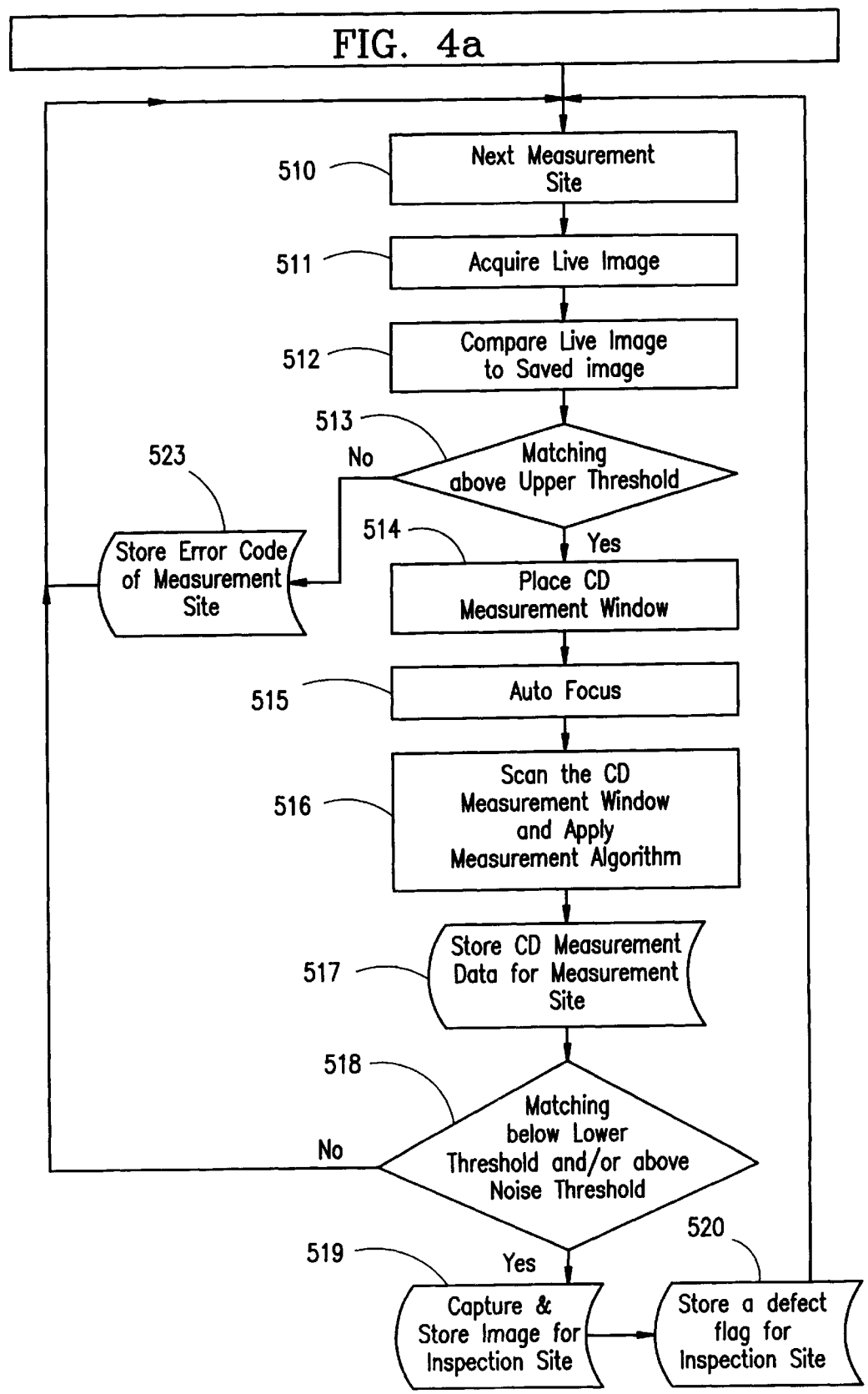

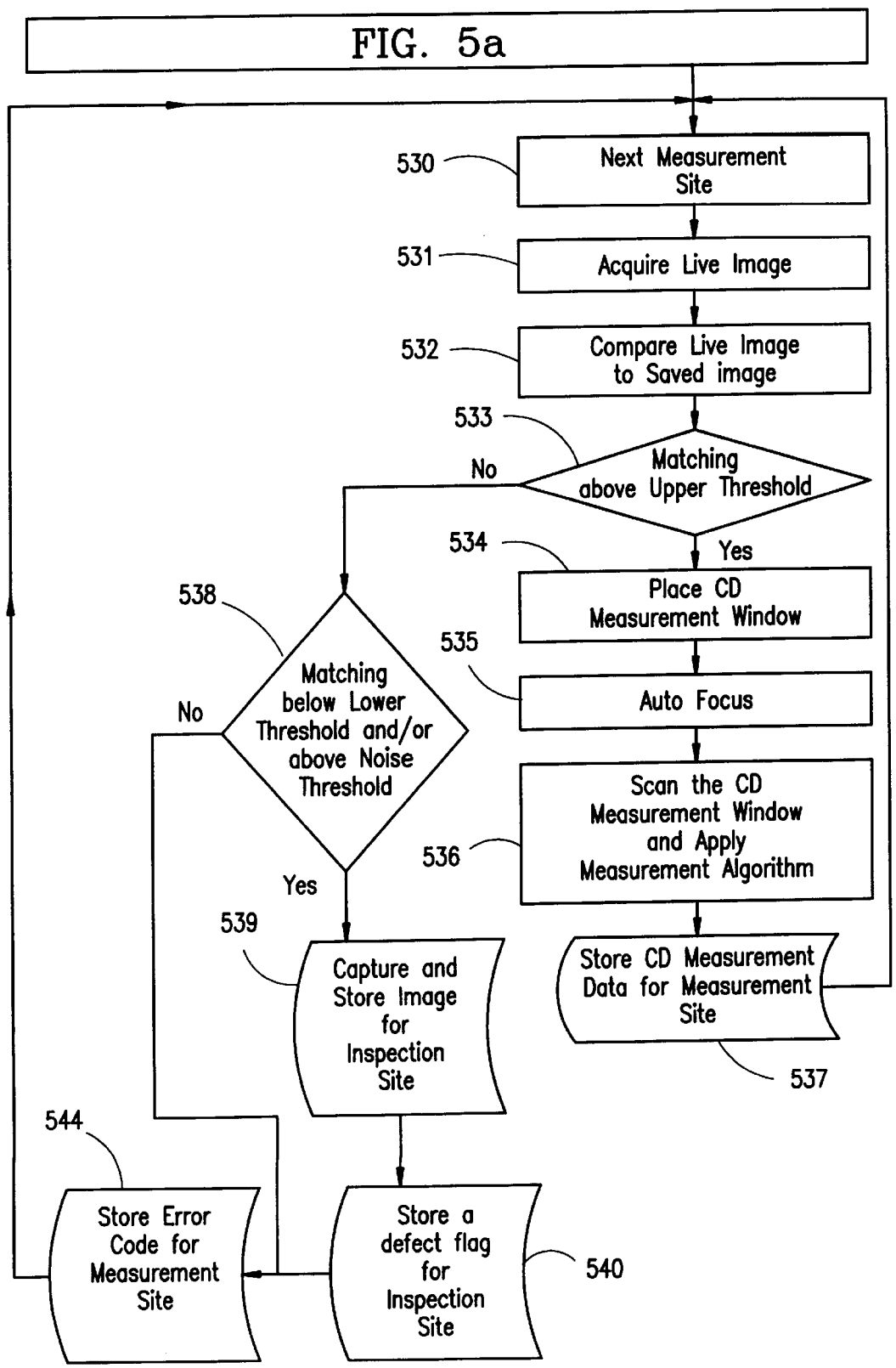

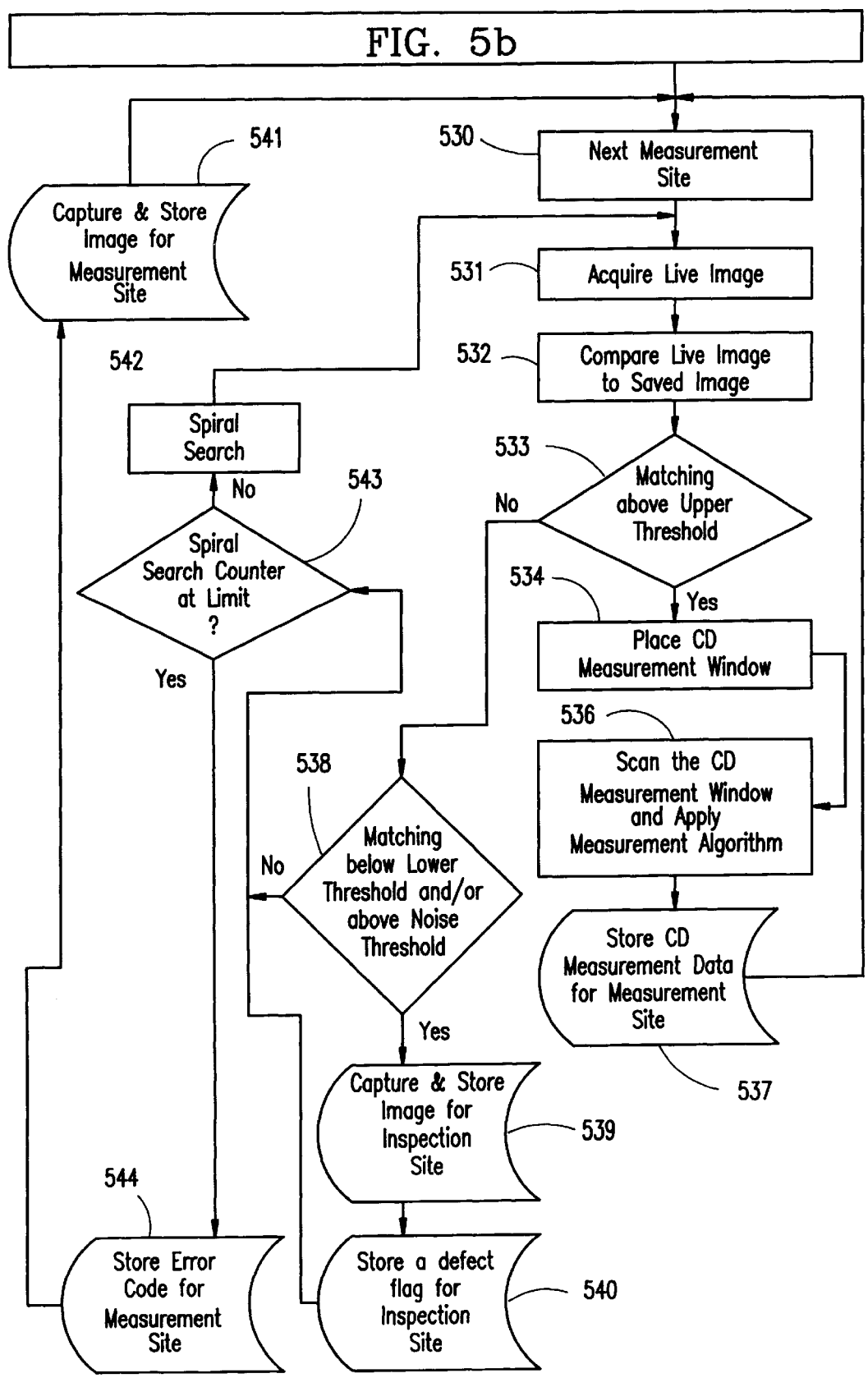

METHOD AND APPARATUS FOR DETECTING DEFECTS IN THE MANUFACTURE OF AN ELECTRONIC DEVICE

This application is a divisional of Ser. No. 09/023,925, filed Feb. 13, 1998, the subject matter of which is incorporated by reference herein.

BACKGROUND OF THE INVENTION

1. Field of the Invention

The invention is directed to the field of fabricating and manufacturing electronic devices. More specifically, the invention is directed to a measurement and detection method and apparatus for detecting defects in the manufacture of an electronic device such as a semiconductor integrated circuit or a wafer composed of a plurality of integrated circuits.

2. Description of Related Art

In the semiconductor industry, there is a continuing movement towards higher integration, density and production yield, all without sacrificing throughput or processing speed. The making of today's integrated circuits (ICs) requires a complex series of fabrication, inspection and testing steps interweaved throughout the entire process to ensure the proper balance between throughput, processing speed and yield. The inspections and tests are designed to detect unwanted variations in the wafers produced, as well as in the equipment and masks used in the fabrication processes. One small defect in either the devices produced or the process itself can render a finished device inoperable.

Many of the inspection steps once done manually by skilled operators have been automated. Automated systems increase the process efficiency and reliability as the machines performing the inspection are more consistent than human operators who vary in ability and experience and are subject to fatigue when performing repetitive tasks. The automated systems also provide greater amounts of data regarding the production and equipment, which enables process engineers to both better analyze and control the process.

One such automated inspection step is known as "pattern inspection." Many different "patterns" appear on both the wafer and the masks used to produce the ICs. Patterns may be repeated areas on a single IC such as test areas, memory areas, shift registers, adders, etc., or, as shown in FIG. 1, the ICs (or dies) themselves may be considered a "pattern" that is repeated throughout the wafer.

Typical pattern inspection systems are image based, as described, for example, in U.S. Pat. Nos. 4,794,646; 5,057,689; 5,641,960; and 5,659,172. In U.S. Pat. No. 4,794,646, for example, the wafer, or part thereof, is scanned and a highly resolved picture or image of the pertinent "pattern" is obtained. This pattern image is compared to other pattern images retrieved from the same or other wafers, or is compared to an ideal image stored in the inspection system database. Differences highlighted in this comparison identify possible defects in the IC or wafer.

Another inspection step that is typically automated in processes today is known as "critical dimension (CD) measurement." On each integration level there is a region or set of patterns or features whose dimensions are critical to the functioning of the entire circuit. A representative pattern is chosen for CD measurements. Examples of CD features include transistor channel length (gate length), transistor channel width, trench depth, step slope, spacing, contact dimensions, etc. Like pattern inspection, CD measurement can be done during several different stages in the fabrication process (e.g., masking, developing, final inspection, etc.).

With the increase in integration, the dimensions to be measured as CDs are so minute that scanning electron microscopes (SEMs) have replaced other optical systems as the tool for performing CD measurements. See, e.g., U.S. Pat. No. 5,109,430. Indeed, SEMs made exclusively for CD measurements are commonplace.

The ability of a viewing system to distinguish detail is related to the wavelength of the light (radiation) used. The shorter the wavelength, the smaller the detail that can be seen. With feature sizes breaking the sub-micron barrier, it is imperative that variations in the lower sub-micron range be detected. One error, even of this small magnitude, may be enough to render the entire IC or wafer useless. Only the SEM provides the capability to detect these variations.

For automated CD-SEMs, fiducial markers on wafers are typically included for the purpose of locating certain features or structures—usually test targets. U.S. Pat. No. 5,109,430, for example, discloses use of fine scale marks fabricated in a pattern in a two-dimensional array to form a target occupying a region of the IC where circuitry is not to be formed, e.g., between bonding pads or in a region interior to the bonding pads. Different patterns on different layers can be used to detect misalignment between layers, as well as measure critical dimensions of the patterns.

These "test targets" are specially designed structures included on the wafer for test purposes only. If the test targets are the correct size and shape, it follows that other semiconductor devices in their proximity will also have the correct size and shape and will therefore function properly. During its scanning of the wafer surface, the CD-SEM compares stored image data of the fiducial wafer markers with the scanned images received from the current position of the wafer under the CD-SEM. Once a "best match" is made, the CD-SEM is in correct position to perform the CD measurement on the intended "test target" for that particular location of the wafer (or IC).

With each new level of integration achieved, a number of new fabrication steps are introduced. This increase is inherently followed by a similar increase in the inspection and testing steps needed to ensure quality control of the products. The increased complexity of the process, however, typically leads to a reduction in throughput or processing speed.

SUMMARY OF THE INVENTION

The invention provides a unique apparatus for and method of detecting defects in an electronic device. In one preferred embodiment, the electronic device is a semiconductor integrated circuit (IC), particularly one of a plurality of IC dies fabricated on a wafer of silicon or other semiconductor material. The defect detection operation is effectuated by a unique combination of critical dimension measurement and pattern inspection techniques. During the initial scan of the surface of the wafer, in an attempt to locate the appropriate critical dimension (CD) feature or element that is to be measured during a CD measurement procedure, a "best fit" comparison is made between a reference feature image and the currently scanned feature image. In addition, a "worst fit" comparison is made between the reference feature image and the scanned feature images. A "worst fit" determination represents pattern distortions or defects in the ICs under evaluation.

The invention thus provides a method and apparatus for detecting defects in an electronic device while scanning for the areas at which critical dimension measurements are to be made, thereby avoiding the need to carry out the otherwise separate steps of defect pattern recognition and CD measurement.

BRIEF DESCRIPTION OF THE DRAWINGS

The foregoing and other features and advantages of the invention will become more apparent from the detailed description of the preferred embodiments of the invention given below with reference to the accompanying drawings in which:

FIGS. 4a and 4b are flowcharts describing the operation of preferred embodiments of the invention;

FIGS. 5a and 5b are flowcharts describing the operation of additional preferred embodiments of the invention;

DETAILED DESCRIPTION OF PREFERRED EMBODIMENTS

The present invention will be described in detail with reference to preferred embodiments illustrated in the accompanying drawing figures. Although these embodiments depict the invention as in its preferred application to a semiconductor device formed in a silicon wafer, it should be readily apparent that the invention has equal application to any type or configuration of semiconductor device (e.g., microprocessor, microcomputer, memory circuit, digital signal processor (DSP), programmable logic array (PLA), etc.) in any type of arrangement (e.g., individual die, packaged die, etc.), as well as any other electronic device (e.g., flat panel displays, liquid crystal displays (LCDs), etc.) that encounters the same or similar problems.

Figure 2:
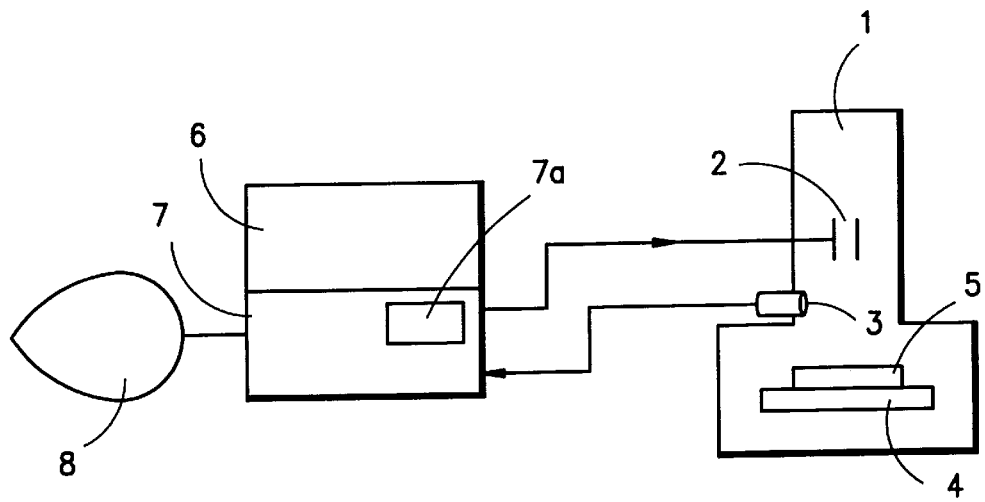
FIG. 2 is a schematic diagram of a SEM in accordance with a preferred embodiment of the invention.

In accordance with a preferred embodiment of the invention, a method and apparatus for detecting defects in the manufacture of an electronic device such as an integrated circuit (IC) on a silicon wafer is provided. In one implementation, a defect detection station, as shown in FIG. 2, can be constructed having a scanning electron-beam microscope (SEM) 1 used for viewing purposes, as is well known in the art. Although the invention is described herein as used during final wafer inspection of the IC dies, it can readily be appreciated that the invention has application to any other stage of manufacturing, e.g., inspection after the initial photomasking and baking of a wafer known as "development inspection," where critical dimension measurements or pattern inspections are contemplated.

SEM 1 is provided with an object support structure 4 in the form of a stage or chuck, which may be moveable or stationary. An object 5 under evaluation such as an IC sample die or a wafer containing many IC dies rests on stage 4. Under control of computer 6, the stage 4 may be moveable in two (X-Y) or three (X-Y-Z) dimensions to facilitate the proper viewing of object 5 (or parts thereof). A deflector 2 and detector 3, whose operations will be described in detail below, are also provided within SEM 1 to assist in the viewing of object 5. An image processor 7, together with its accompanying image memory 7a are provided to process the image signals output by SEM 1 and transform the signals into visual representations or data which can be viewed on a display monitor 8 (e.g., cathode ray tube (CRT)) or used for processing in computer 6.

In operation, SEM 1 uses a finely focused electron beam directed by deflector 2, preferably under the control of computer 6, to scan the surface of the object 5 resting on stage 4, typically in two dimensions (X-Y). For the purposes of discussion only, it will be assumed herein that the object 5 under evaluation is a silicon wafer having a plurality of semiconductor integrated circuit dies fabricated thereon. The electrons striking the semiconductor surface of object 5 collide with inner shell electrons of the object atoms causing inelastic collisions of low energy emitting so-called "secondary electrons" which are serially detected by detector 3.

The detected electron current is output as an image signal to computer 6 and image processor 7 where an image representative of the surface of the object 5 can be formed based on the image signal. This image is stored in image memory 7a and can be viewed on monitor 8 or otherwise processed by computer 6. The high resolution of the image is attributed to the small diameter (e.g., several nanometers) of the electron beam illuminator. The visual contrast achieved in the image originates mostly from variations in the extent of the secondary electron emissions from the topographic features of the surface of the object 5.

Figure 6A:
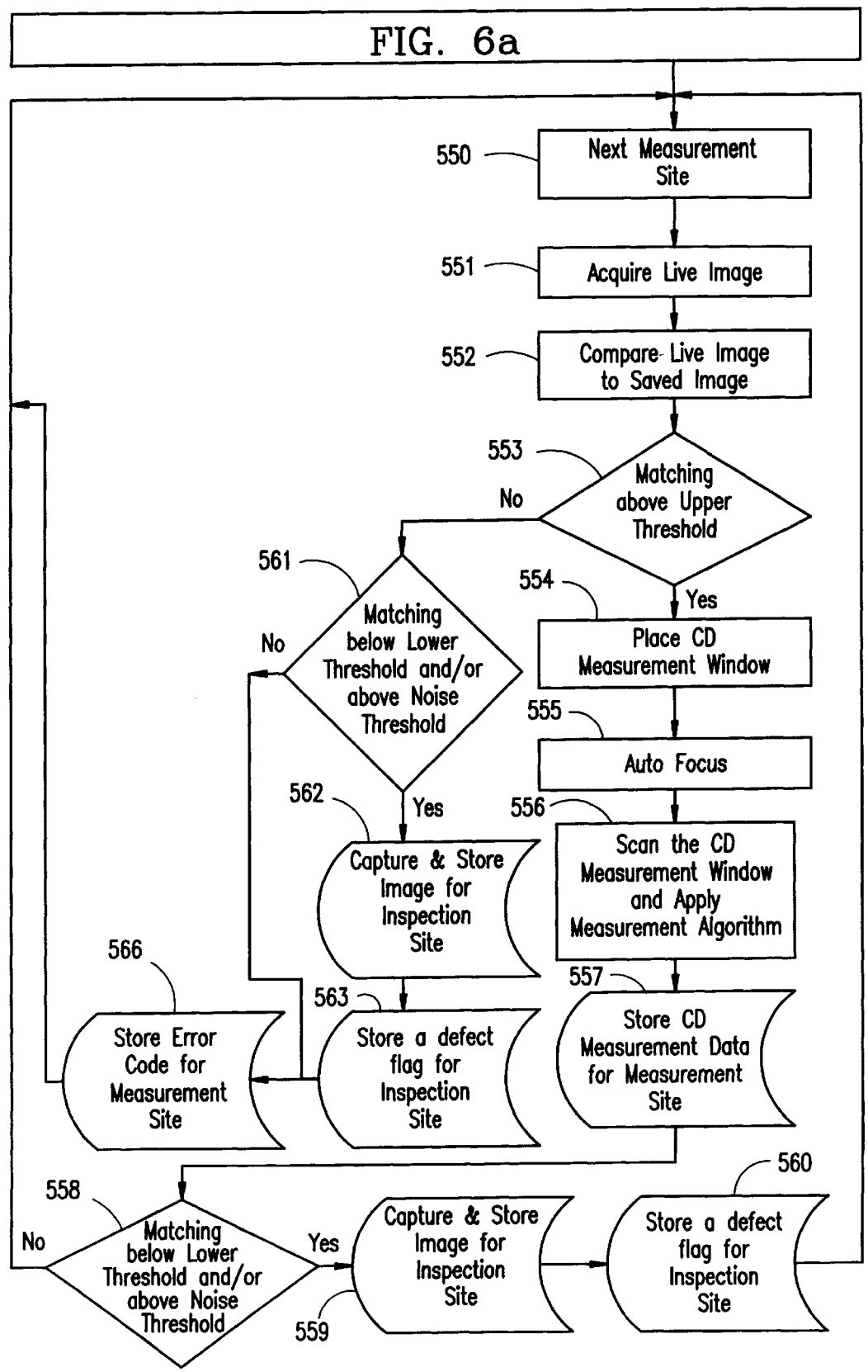
FIGS. 6a and 6b are flowcharts describing the operation of yet additional preferred embodiments of the invention.
Figure 6B:
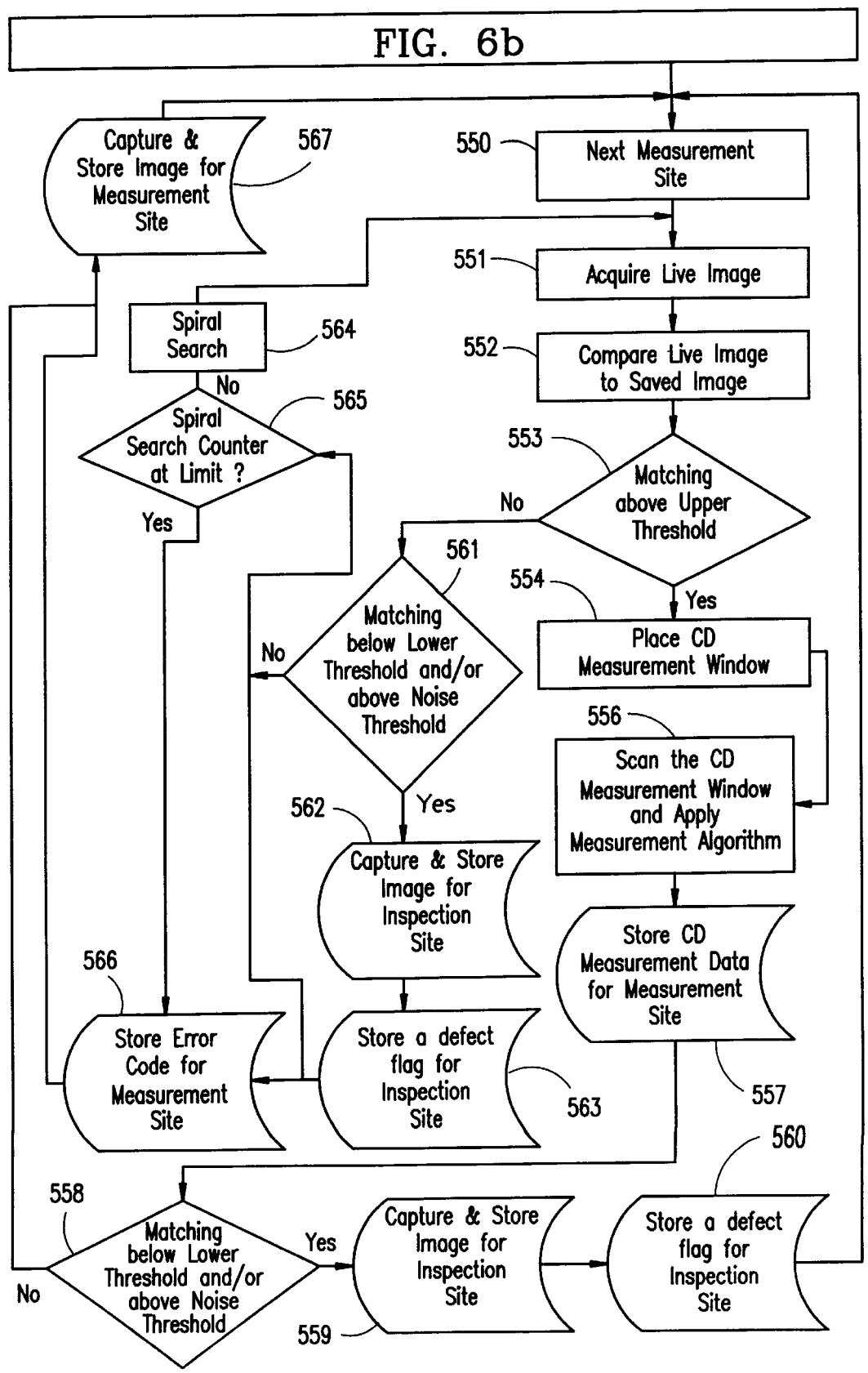
Figure 7:
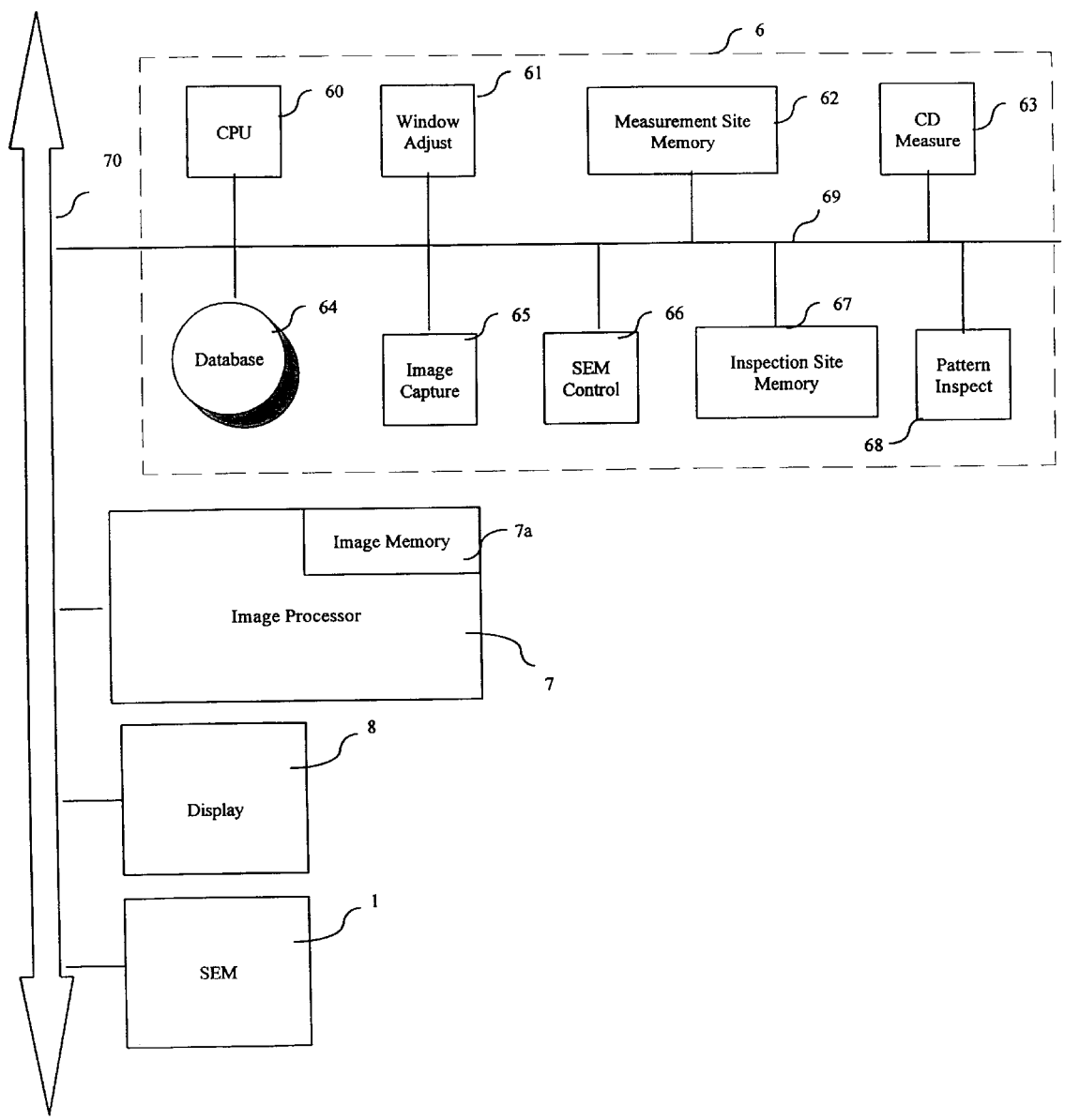
FIG. 7 is a block diagram of an apparatus in accordance with an preferred embodiment of the invention.

As shown in FIG. 7, the defect detection station (FIG. 2), in accordance with one preferred embodiment of the invention, incorporates within computer 6 a collection of modules such as central processing unit 60, a window adjust unit 61, a measurement site memory 62, a CD measurement unit 63, a database 64, an image capture unit 65, a SEM control unit 66, an inspection site memory 67, a pattern inspect unit 68, and local bus 69. These modules may either be hardware components, software components, or a combination of hardware/software components constructed as known in the art to accomplish the functions described herein. The components may be implemented individually or together as a single group (e.g., a single computer program run on a computer processor or the like such as CPU 60). Indeed, in one example, the invention may be implemented in a conventional CD-SEM such as the "IVS-200" made by IVS, Inc., the "Opal 7830si" made by Applied Materials, or the "S-8820/8620" made by Hitachi, by modifying the computer program used by the control computer within the SEM such that the control computer implements in software the functions of each module described herein and the operations performed in the flowcharts of FIGS. 4a through 6b. Individual ones of the components may also be combined into smaller groups, e.g., CD measure 63 and pattern inspect 68 may be combined with CPU 60, while measure site memory 62 and inspection site memory 67 can be combined. These modules in computer 6, together with SEM 1, image processor 7, image memory 7a, and display 8 are operatively connected to one another to facilitate the operation of various preferred embodiments of the invention, as will be described below.

Figure 1:
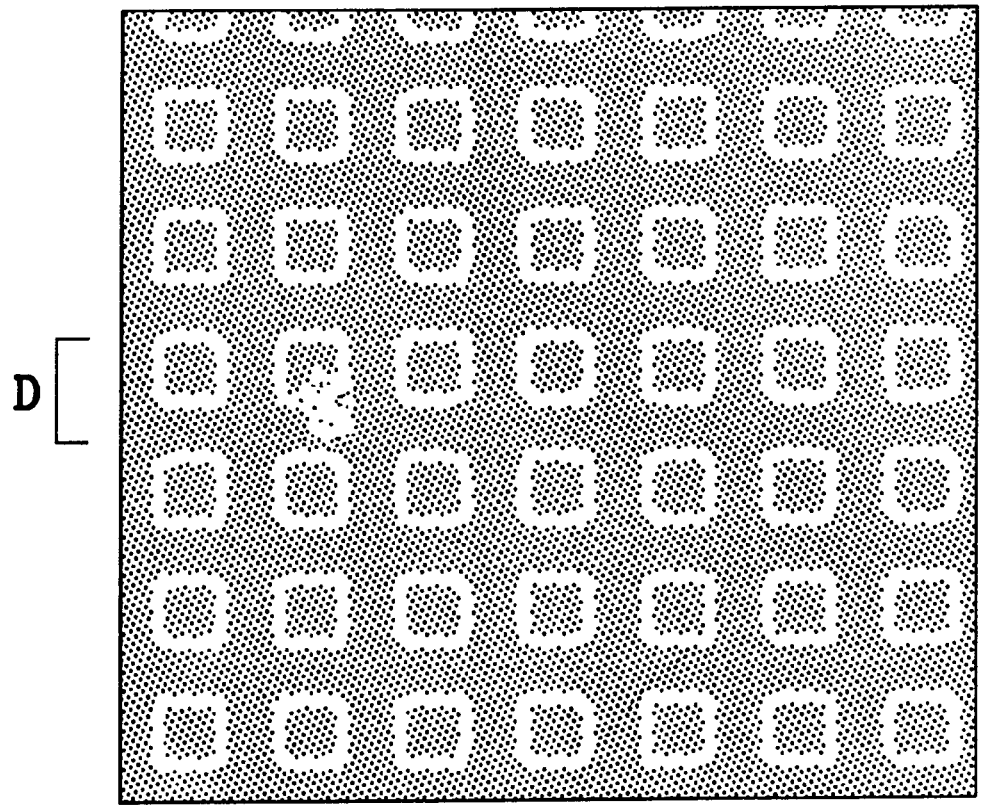
FIG. 1 illustrates patterns of integrated circuit dies formed on a silicon wafer.

In detecting defects in the object 5, the invention relies on a combination of pattern inspection and critical dimension measurement techniques. In particular, the invention relies on the use of a SEM, which performs critical dimension measurements, to perform the pattern inspection while the SEM is performing its function of CD measurement. As the SEM is searching for the "best match" image of a fiducial wafer marker, the SEM simultaneously searches for differences between stored reference patterns and the image patterns detected from the current wafer. Where the SEM detects a significant aberration in the current image pattern, as shown as pattern 44b in FIG. 3 (as well as in region "D" on FIG. 1), the SEM determines that a defect has been found. As an alternative to the fiducial wafer markers, other CD features or other components of an IC or wafer may be used for measurement such as transistor channel length (gate length), transistor channel width, trench depth, step slope, spacing, contact dimensions, etc.

Figure 3:
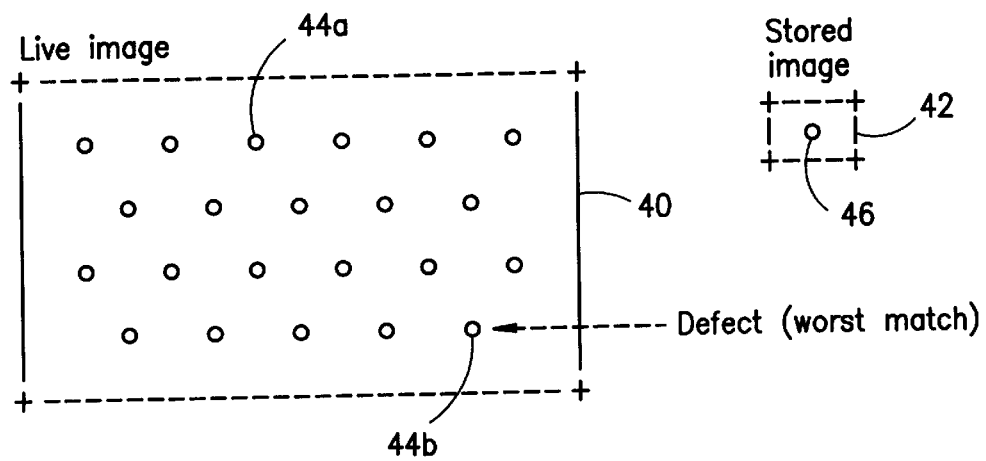
FIG. 3 shows images captured by a SEM in accordance with a preferred embodiment of the invention.

The foregoing operation is more fully described with reference to the flowcharts in FIGS. 4a, 4b, 5a, 5b, 6a and 6b, which are executed, for example, by the SEM computer and with each representing a respective preferred embodiment of the invention. In the first of these embodiments, depicted in FIG. 4a, SEM control 66 (FIG. 7) controls the deflector 2 and stage 4 to permit SEM 1 to scan one or more measurement sites of the wafer 5 (S10). The measurement site is preferably one of several different regions or sections of an IC die fabricated on the wafer 5 (although it may also be one of several sections of wafer 5 made up of a plurality of IC dies). As shown in FIG. 3, each measurement site 40 preferably contains a plurality of cells 44a, 44b in a semiconductor memory device. The sites may alternatively contain a plurality of circuit components or features of the IC, or they may even be a plurality of IC dies. In an alternative embodiment, "test target" regions may serve as measurement sites. "Test targets" are made up of non-functional structures that are fabricated in portions of the wafer or IC itself where no functional circuitry is placed, as described in U.S. Pat. No. 5,109,430, which is incorporated herein by reference in its entirety.

SEM 1 then initiates acquisition or capture (S11) of a "live" image of the image area. For purposes of illustration only, we assume that the "live" image is over a plurality of cells, e.g., 44a, 44b, etc. in a semiconductor memory, as shown in FIG. 3. To achieve this image capture, computer 1 relies on detector 3 to sense the secondary electrons emitted from the area on wafer 5. Image capture module 65 takes control of the transmission of the image signal output from detector 3 to image processor 7, as well as the storage of the "live" image, as represented by the image signal, in image memory 7a.

Central processing unit (CPU) 60 then retrieves a stored image 42 (FIG. 3) of a pattern or feature 42 that serves as the reference (or "ideal") pattern that can be used as a template. In the preferred embodiment, the reference pattern is an image of a semiconductor memory cell created based on design rules, etc. developed by manufacturing personnel and stored in database 64 (or some other storage device). The image 42 may also be taken from a calibrating "reference" wafer, from other in-line wafers, or even from adjacent IC dies or measurement sites on the same wafer 5, as can be recognized by those of ordinary skill in the art.

CPU 60 then performs in Step S12 a comparison between all of the cells, including cells 44a and 44b, of the measurement site 40 and the reference cell 46 of stored image 42 to determine the similarities (or dissimilarities) between the individual measurement site cells such as 44a and 44b, and reference cell 46, and to produce a comparison score reflecting the similarities/dissimilarities. Any known comparison algorithm or calculating device may be utilized to produce a comparison score that provides some indication of similarities/dissimilarities of the images. For example, CPU 60 may be programmed to calculate an image quotient by dividing the number of pixels found to be the same between the live and reference sites by the total number of pixels available. CPU 60 uses the comparison score thus calculated to determine the "best fit" between each of the "live" measurement cell sites and the stored measurement site 46.

The "best fit" may be found by determining whether any of the comparison scores for an individual measurement site under evaluation exceeds an upper threshold (S13). In particular, the "best fit" may be found by determining whether the comparison score for an individual measurement site cell, e.g., 44a, under evaluation exceeds an "upper threshold" value, which is preferably assigned by the operator, engineer, or designer and stored in the database 64 or other program memory prior to use on the manufacturing floor. (S13).

In the preferred embodiment, during step S12, CPU 60 will compare the image of an individual cell of measurement site 40 with the reference cell 46 of reference site 42 stored in database 64. For each individual cell considered, CPU 60 will calculate a comparison score until CPU 60 detects a comparison score that exceeds the "upper threshold" value. The first time the "upper threshold" is exceeded based on one of the cells, e.g., 44a, 44b, CPU 60 will send an enable signal over local bus 69 to CD measure unit 63, which is operative to perform a CD measurement on the feature or structure appearing at the current measurement site cell 44a (S13). If CPU 60 has compared all of the cells in measurement site 40 to the reference cell 46 and found that none of the calculated comparison scores exceed the "upper threshold" value (S13), the process turns to step S23, which will be described later below.

Where the "upper threshold" value has been exceeded by a cell site, however, a CD measurement procedure begins in step S14. To accomplish the CD measurement, window adjust module 61 places a CD measurement window around the current measurement site, e.g. 44a (S14). Preferably, SEM control 66 directs stage 4 to reposition wafer 5 and automatically focus (S15) SEM 1 to permit CD measurements to be made, in a manner well known in the art. Using image capture module 65, together with image processor 7 and image memory 7a, the surface of the wafer 5 within the CD measurement window is scanned into image memory 7a, and the CD measurements taken by CD measure unit 63 (S16). CD measure unit 63 may employ any CD measurement algorithm or technique known in the art to produce the dimensions or sizes of the measurement feature. U.S. Pat. No. 5,555,319, for example, which is incorporated by reference herein in its entirety, illustrates one such CD measurement technique that may be utilized in CD measurement unit 63. The CD measurement data derived is then stored in measurement site memory 62 (S17).

After the CD measurements are taken, CPU 60 next determines whether any of the above-calculated comparison scores falls below a "lower threshold" (S18). During the comparison score calculations in step S12, CPU 60 stores in an internal/external CPU memory (not shown), database 64, or any other storage unit, the calculated comparison scores for each cell of the measurement site 40 being evaluated. In step S18, CPU 60 reviews the stored comparison scores and determines which, if any, fall below the "lower threshold" value. In the case where comparison scores for all of the cells 44a, 44b were not calculated in step S12 because a cell was reached which exceeded the upper threshold in step S13, CPU 60 proceeds to calculate the remainder of the comparison scores for the remainder of cells in measurement site 40.

As with the "upper threshold," value, the value assigned to the "lower threshold" is preferably predetermined prior to use on the manufacturing floor. Where CPU 60 finds that any of the comparison scores falls below the "lower threshold," CPU 60 directs image capture module 65 to capture the current "live" image 40 or, alternatively, only the image of the defective cell 44*b*, and store the image in inspection site memory 67 (S19). Subsequently, CPU 60 stores a defect flag corresponding to the defect detected in inspection site memory 67 (S20). CPU 60 then causes the basic process flow to repeat for the next measurement site 40 (S10).

In the event, in step S18, CPU 60 finds that none of the comparison scores fall below the "lower threshold" value for any of cells 44*a*, 44*b*, CPU 60 restarts the process again with the next measurement site (S10).

Where CPU 60, in step S13, finds that none of the comparison scores exceed the "upper threshold" value, CPU 60 may cause an "error code" to be stored in measurement site memory 62 (S23) associated with the measurement site 40 under evaluation. The process may then begin again with the next measurement site (S10).

In an alternative embodiment, the "upper threshold" (described above) may be dynamically assigned based on the relative comparison scores of other measurement site cells in the same live image 40, or based on other live images on the same wafer, or based on completely different wafers. For example, CPU 60 may scan and calculate comparison scores for all the measurement site cells in one particular live image 40. The CPU 60 would then assign as the "upper threshold" value a number just below the comparison score that represents the highest similarity between live image measurement site cell, e.g., 44*a*, 44*b*, and reference site cell 46. The CPU 60 would then locate the measurement site that exceeds this threshold, as in step S13.

Alternative embodiments may also rely on a "noise threshold" value to provide additional checks on the quality of the device produced or the process itself. Often stray or spurious noise signals attributed to operation of the SEM or the environment surrounding the SEM cause imperfections to appear in the scanned image even though there are no imperfections in the underlying device under inspection. These noise signals must be distinguished from the distortions or defects actually present in the patterns found on the electronic device. By assuming that a small portion of the comparison score will be affected by the noise level, and taking this noise level into account when determining whether a defect exists, the effects of the noise on the detection system can be diminished. Thus, step S18, for example, may be modified to require that the comparison score be above the "noise threshold" as an added condition, as shown in FIGS. 4*a* and 4*b*.

As another alternative, in step S18, should CPU 60 determine that a calculated comparison score falls below the "lower threshold" value, CPU 60 will send an enable signal via local bus 69 to pattern inspect unit 68 to initiate a pattern inspection procedure using any of the known inspection algorithms or techniques in the art. U.S. Pat. No. 4,556,317, for example, which is incorporated by reference herein in its entirety, illustrates one such pattern inspection technique that may be utilized in pattern inspect unit 68. After conducting the procedure, should pattern inspect unit 68 then determine the presence of a pattern distortion or defect, the "defect flag" step (S20) can then be performed, as described above.

Figure 4B:
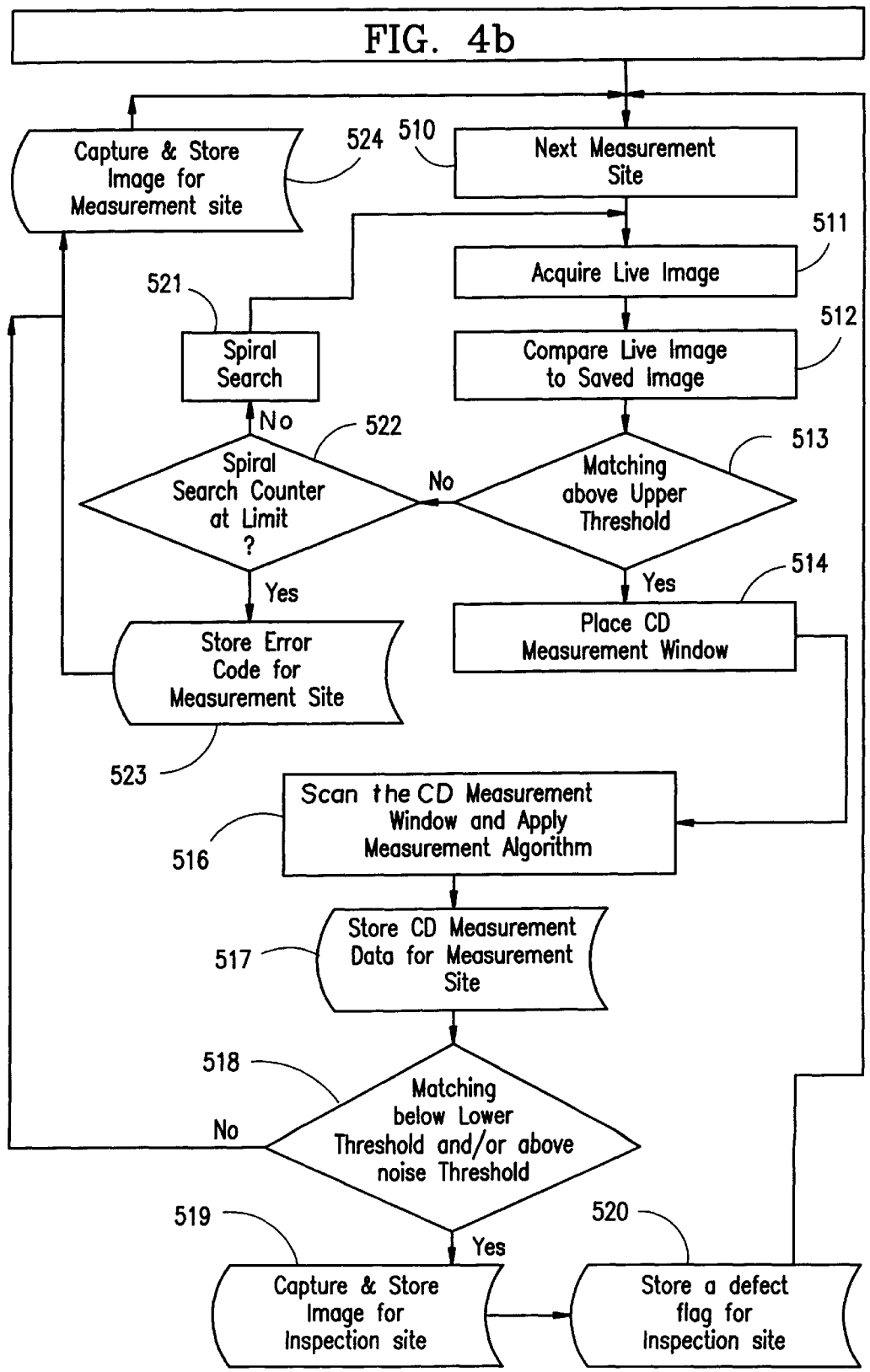

FIG. 4*b* illustrates another embodiment of the invention. Many of the steps shown in FIG. 4*a*, as described above, are retained and bear the same reference numerals in FIG. 4*b*. The automatic focus step (S15) of FIG. 4*a*, however, is bypassed altogether in the embodiment shown in FIG. 4*b*, and the process proceeds from step S14 directly to step S16. Also, where CPU 60 finds that none of the comparison scores calculated exceed the "upper threshold" in step S13, CPU 60 may perform an alignment check in accordance with the embodiment of FIG. 4*b* to verify that the reference measurement site cell 46 is in the best alignment with the measurement site cell currently under evaluation to compare the cells for similarities/dissimilarities. The alignment check may be performed using an internal software search or some external module.

In this embodiment, a searching routine known as a "spiral search," shown as steps S21 and S22, is performed a predetermined number of times, as tracked by spiral search limit counter (S22). The spiral search moves the image of the measurement site under scrutiny slightly in an attempt to locate a cell area which has a comparison score which exceeds the threshold in step S13. A typical "spiral search" which may be implemented in the invention is shown and described in U.S. Pat. No. 5,621,813, which is herein incorporated by reference in its entirety. Alternative search techniques, e.g., linear search, circular search, etc., may also be used in lieu of the spiral search (S21) technique described herein. Examples of such search techniques can be found in U.S. Pat. No. 5,487,172, which is also herein incorporated by reference in its entirety. If all of the comparison scores remain below the "upper threshold" value after a number of spiral search attempts are made, as tracked by spiral search counter in step S22, an error code is stored in measurement site memory 62 (S23) and the "live" image is captured and stored in the measurement site memory 62 (S24) before the process moves to a new measurement site (S10).

In another preferred embodiment, a similar basic process flow chart is shown in FIG. 5*a*. Indeed, steps S30–S37 in FIG. 5*a* are identical to steps S10–S17 of FIG. 4*a*. However, instead of performing a pattern inspection routine after the CD measurements are made, as in steps S18, S19, and S20 shown in the embodiment of FIG. 4*a*, the same steps (shown in FIG. 5*a* as S38, S39 and S40) are now located after the step of determining that the comparison score does not exceed the "upper threshold" (S33). Also, the step of storing a defect flag in inspection memory (S40) shown in FIG. 5*a* does not proceed immediately to the next measurement site, as in FIG. 4*a*. Instead, in the embodiment of FIG. 5*a*, an error code for the measurement site is stored in measurement site memory 62 (S44), after which the process moves to the next measurement site (S20).

The embodiment shown in FIG. 5*b* is similar to that shown in FIG. 5*a*. The essential difference resides in the presence of an alignment check procedure, preferably in the form of a spiral search (S42, S43), in FIG. 5*b*, that can be made prior to storing an error code in the measurement site memory 62 (S44). The embodiment further includes the step (S41) of capturing and storing the image in measurement site memory 62 after the error code is stored.

In the embodiment of FIG. 6*a*, much of the same steps making up FIG. 5*a*, e.g., steps S30–S44, are identical to the steps used in FIG. 6*a*, e.g., steps S50–S67, respectively. The embodiment shown in FIG. 6*a* differs only by the addition of steps S58, S59 and S60. These steps follow the CD measurement procedures (steps S54 through S57). These added steps provide for an additional opportunity to perform pattern inspection using the same procedures found in steps S61, S62 and S63. Thus, the embodiment of FIG. 6*a* is a variation which combines the steps of both FIG. 4*a* and FIG. 5*a* to form another preferred embodiment of the invention.

Similarly, the embodiment of FIG. 6*b* is much like the embodiment of FIG. 5*b* in that steps S50 through S67 of FIG. 6b are identical to steps S30 through S44 of FIG. 5b. The embodiment of FIG. 6b, however, adds steps S58, S59 and S60, as described above.

The invention described herein provides a method and apparatus for detecting defects in an electronic device, such as an integrated circuit arrayed on a silicon wafer, while also scanning a surface area for CD measurement and without sacrificing throughput or processing speeds.

While the invention has been described in detail in connection with the best mode of the invention known at the time, it should be readily understood that the invention is not limited to any of the specified embodiments. Rather, the invention can be modified to incorporate any number of variations, alterations, substitutions or equivalent arrangements not heretofore described, which fall within the spirit and scope of the invention.

For example, any one or more of the modules 60–69 (FIG. 7) contained in computer 6 may be incorporated into one or more components (e.g., SEM 1, image processor 7, etc.) of the defect detection station (FIG. 2). Either local bus 69, main bus 70, or any connections to either bus may be replaced or supplemented by a remote local area network (LAN), intra/internet, or any other wired/wireless communication link that provides for communication between at least two points, as known in the art. The database 64 may be separated from computer 6 and connected by main bus 70 locally, or remotely through permanent or request-based (e.g., dial-up, etc.) communications links known in the art. The CD measure unit 63 (FIG. 7) may be any other type of measuring (or metrological device) known in the art for taking measurements of the dimensions or sizes of features, elements, components, etc. of an electronic device.

Regardless of the modifications later contemplated by those of ordinary skill in the art, the nature, spirit and scope of the invention is only limited by the scope of the claims appended hereto.

What is claimed is:

1. A dimension measurement station for measuring dimensions of an integrated circuit (IC), the measurement station comprising:

a chuck for supporting an IC during measurement;

an image detector, operatively coupled to said chuck, which operates to detect an image of the IC, and to output a detection signal representative of the image detected;

an image memory, operatively coupled to said image detector, which stores the image detected by said image detector;

a processor, operatively coupled to said image memory, which compares the detected image in said image memory to a predetermined image, and accumulates similarities between each detected image and the predetermined image, wherein said processor generates a measurement signal for a detected image which has a maximum number of similarities, and generates an inspection signal for a detected image which has a minimum number of similarities;

a metrological device, operatively coupled to said processor, responsive to the measurement signal generated by said processor to take measurements of a detected image of the IC having said maximum number of similarities;

a pattern matching device, operatively coupled to said processor, responsive to the inspection signal generated by said processor to identify a detected image having said minimum number of similarities as representing a pattern defect in said IC.

2. The dimension measurement station as recited in claim 1, further comprising:

a scanning electron-beam microscope (SEM) focused on a portion of the IC; and wherein said processor further comprises a chuck controller for controlling movement of said chuck in at least two dimensions so as to permit said SEM to individually focus on respective ones of a plurality of circuit elements on the IC, wherein said processor outputs a measurement signal when said SEM is focused on one of the plurality of circuit elements on the IC which produces a detected image with a maximum number of similarities relative to the predetermined image.

3. The dimension measurement station as recited in claim 1, wherein the IC is one of a plurality of fabricated devices in an array on a semiconductor wafer, and wherein the predetermined image corresponds to an adjacent one of the plurality of fabricated devices on the semiconductor wafer.

* * * * *